United States Patent [19]

Hansen

[11] Patent Number: 5,474,657
[45] Date of Patent: Dec. 12, 1995

[54] PREPARATION OF F-ALKYL F-ISOBUTYL ETHERS BY ELECTROCHEMICAL FLUORINATION

[75] Inventor: John C. Hansen, Lakeland, Minn.

[73] Assignee: Minnesota Mining and Manufacturing Company, St. Paul, Minn.

[21] Appl. No.: 194,255

[22] Filed: Feb. 10, 1994

[51] Int. Cl.$^6$ ..................................................... C25B 3/08
[52] U.S. Cl. ........................................... 204/59 F; 204/81
[58] Field of Search ............................... 204/59 R, 59 F, 204/72, 81

[56] References Cited

U.S. PATENT DOCUMENTS

| | | | |
|---|---|---|---|
| T983,009 | 6/1979 | Treat | 260/652 P |
| 2,519,983 | 8/1950 | Simons | 204/62 |
| 2,713,593 | 7/1955 | Brice et al. | 260/535 |
| 3,306,940 | 2/1967 | Halliwell | 260/653.3 |
| 3,950,235 | 4/1976 | Benninger | 204/59 F |
| 3,962,348 | 6/1976 | Benninger et al. | 260/615 F |

FOREIGN PATENT DOCUMENTS

| | | | |
|---|---|---|---|
| 0444822A1 | 2/1991 | European Pat. Off. | C07C 381/00 |
| 0455399A2 | 4/1991 | European Pat. Off. | C25B 3/08 |
| 879057 | 10/1961 | United Kingdom . | |

OTHER PUBLICATIONS

Koshar et al., "The Addition of Alcohols to Octafluoroiso-butene", Journal of American Chemical Society, vol. 79 (Apr. 5, 1957), pp. 1741–1744.

Chem. Abs., vol. 70, 15833 (1969) no month.

"Perfluorocarbon Ether Compounds Prepared by Electrolyzing a Fluorocarbon Polyether in Hydrofluoric Anhydride in the Presence of an Inert Gas," Agency of Ind. Sci. Tech., Derwent Pub. Feb. 27, 1978.

T. Abe and S. Nagase, "Electrochemical Fluorination (Simons Process) As a Route to Perfluorinated Organic Compounds of Industrial Interest" in *Preparation, Properties, and Industrial applications of Organofluorine Compounds*, ed. R. E. Banks (Holsted Press, 1982) pp. 19–43 (no month).

J. Burdon and J. C. Tatlow, "The Electrochemical Process for the Synthesis of Fluoro–Organic Compounds" in *Advances In Fluorine Chemistry*, vol. 1 (1960) pp. 130–165 (no month).

R. D. Chambers and B. Grievson, "A New Route to Perfluorinated Ethers" in *Journal of Fluorine Chemistry*, vol. 25 (1984) pp. 523–525 (no month).

R. D. Chambers et al., "Free–Radical Chemistry, Part 8[1]. Electrochemical Fluorination of Partly Fluorinated Ethers" in *Journal of Fluorine Chemistry*, vol. 49 (1990) pp. 409–419 (no month).

W. V. Childs et al., "Anodic Fluorination" in *Organic Electrochemistry: An Introduction and a Guide*, ed. H. Lund and M. Baizer, Third Edition (Marcel Dekker, Inc., 1991) pp. 1103–1127 (no month).

H–N Huang et al., "Synthesis of Unusual Perfluorocarbon Ethers and Amines Containing Bulky Fluorocarbon Groups: New Biomedical Materials" in *Journal of Organic Chemistry* 53 (1988) pp. 78–85 (no month).

Y. Inouye et al., "2–Hydryl–2–(F–Methyl)–F–Propanoyl Fluoride as a Useful Building Block for the Synthesis of Trifluoromethylated Heterocyclic Compounds. Synthesis of 1,3–Dimethyl–2, 3–Dihydro–5–(F–Methyl)–6–Fluoro–2–Thioxo–4(1H)–Pyrimidinone and 1,3–Dimethyl–5–(F–Methyl)–6–Fluoro–2,4(1H,3H)–Pyrimidinedione" in *Journal of Fluorine Chemistry*, vol. 27 (1985) pp. 379–384 (no month).

Y. Inouye et al., "Synthetic Utilization of Methyl 2–(F–Methyl)–2–Hydryl–F–Propyl Ether, Part III[1]. A Simple One–Pot Preparation and Derivatization of 2–Alkylthio–5–(F–Methyl)–6–Fluoro–3, 4–Dihydro–4(3H)–Pyrimidinones" in *Journal of Fluorine Chemistry*, vol. 35 (1987) pp. 275–285 (no month).

S. Nagase, "Electrochemical Fluorination" in *Fluorine Chemistry Reviews*, vol. 1(1) 1967, pp. 77–106 (no month).

T. Ono et al., "Synthesis of Perfluorochemicals for Use as Blood Substitutes, Part II: Electrochemical Fluorination of Partly Fluorinated Compounds" in *Journal of Fluorine Chemistry*, 27 (1984) pp. 333–346 (no month).

Fluorine Chemistry, edited by Dr. J. H. Simons, Fluorine Laboratories, The Pennsylvania State College, State College, Penna, vol. 1, 1950 Academic Press Inc., Publishers New York, N.Y. (no month).

*Primary Examiner*—Kathryn Gorgos
*Assistant Examiner*—Edna Wong
*Attorney, Agent, or Firm*—Gary E. Griswold; Walter N. Kirn; Eloise J. Maki

[57] ABSTRACT

A method for the preparation of fluoroalkyl fluoroisobutyl ethers is disclosed. Such ethers are prepared by fluorinating, in an electrochemical cell, a solution comprising an adduct of perfluoro-isobutene and an aliphatic alcohol.

8 Claims, No Drawings

PREPARATION OF F-ALKYL F-ISOBUTYL ETHERS BY ELECTROCHEMICAL FLUORINATION

This invention relates to the electrochemical fluorination of perfluoro-olefin adducts of aliphatic alcohols to produce fluorinated alkyl ethers. In another aspect, it relates to the production of fluorinated-alkyl fluorinated-isobutyl ethers by electrochemical fluorination. In a further aspect, it relates to the production of fluorinated alkyl (e.g., methyl or ethyl) penta- or hexafluoro-2-(trifluoromethyl)propyl ethers. In another aspect, it relates to fluorinated branched ethers.

Due to its extreme toxicity and high volatility, perfluorisobutene, $(CF_3)2C=CF_2$, or "PFIB," has not been utilized much as a raw material; but it can be converted to a less harmful methanol adduct, methyl 2-hydryl-2-(fluoromethyl)-fluoropropyl ether, $(CF_3)_2CHCF_2OCH_3$, as pointed out by Y. Inouye et al. in *Jour. of Fluorine Chemistry*, 35 (1987) 275–285. And R. J. Koshar et al., *Jour. of American Chem. Soc.*, 79 (1957) 1741–1744, describes the addition of various aliphatic alcohols, such as methanol and ethanol, to PFIB to afford as the main reaction products the corresponding saturated ethers of the type $(CF_3)_2CHCF_2OR$, along with unsaturated ethers of the type $(CF_3)_2C=CFOR$.

PFIB is a major by-product in the manufacture of hexafluoropropene, Inouye et al., supra. And U.S. Defensive Publication T983,009 (Treat), dated Jun. 5, 1979, citing references, describes a variety of conditions underwhich the formation of PFIB occurs. The latter publication also describes a process for converting toxic PFIB in a mixture of fluorine-containing compounds into a relatively nontoxic ether by contacting the mixture with a solution of HF and/or HCl in methanol.

U.S. Pat. No. 3,962,348 (Benninger et al.) describes an electrofluorination process to produce certain hydrogen-free perfluoro-alkyl ethers from partially-fluorinated perfluoro-olefin adducts of aliphatic alcohols. R. D. Chambers et al., in *Jour. of Fluorine Chemistry*, 49 (1990) 409–419, describes electrochemical fluorination of certain partially-fluorinated cyclic adducts to give corresponding perfluoro-ethers and states that adducts of acyclic ethers are less efficiently fluorinated.

H–N. Huang et al., in *Jour. Organic Chemistry*, 53 (1988) 78–85, describes synthesis of a few branched ethers, such as perfluoro(tert-butyl methyl ether) and perfluoro(isobutyl methyl ether) byproduct, by direct fluorination of their hydrocarbon analogues.

In one aspect, the present invention provides a process for the production of fluoro-alkyl fluoro-isobutyl ether compounds or composition by fluorinating in an electrochemical cell a solution comprising an adduct of perfluoro-isobutene and aliphatic alcohol (e.g., an alkanol such as methanol or ethanol) in anhydrous hydrogen fluoride at concentrations and under temperature and pressure conditions sufficient to fluorinate to desired degree the adduct to the desired fluoro-alkyl fluoro-isobutyl ether compound or composition, such as a perfluoroalkyl pentafluoro-2-(perfluoromethyl)propyl ether or composition comprising a predominant amount thereof, which can be efficiently produced in high yield and high purity.

The adduct starting material that is electrochemically fluorinated, according to this invention, is preferably that produced by reacting methanol with the toxic PFIB byproduct waste stream resulting from the manufacture of hexafluoropropene. The resulting less harmful methanol adduct thereof comprises predominantly the saturated adduct ether, viz., methyl pentafluoro-2-(perfluoromethyl)propyl ether, $(CF_3)_2CHCF_2OCH_3$, and minor amounts of the unsaturated adduct ethers, viz., methyl tetrafluoro-2-(perfluoromethyl)-1-propenyl ether, $(CF_3)_2C=CFOCH_3$, and methyl tetrafluoro-2-(perfluoromethyl)-2-propenyl ether, $CF_2=C(CF_3)CF_2OCH_3$. (As used herein, the terms "predominantly" and "major" mean greater than 50 weight percent, and "minor" means less than 50 weight percent.) The electrochemical fluorination ("ECF") of such PFIB-methanol adduct product according to this invention will produce an ECF reaction product comprising predominantly the fully-fluorinated ether, perfluoromethyl hexafluoro-2-(perfluoromethyl)propyl ether, $(CF_3)_2CFCF_2OCF_3$, and a minor amount of the partially-fluorinated ether, perfluoromethyl pentafluoro-2-(perfluoromethyl)propyl ether, $(CF_3)_2CHCF_2OCF_3$, which can also be named as 2-hydry-l(or hydro)-2-($\underline{F}$-methyl)-$\underline{F}$-propanol fluoride (where "$\underline{F}$" is the oft-used abbreviation or symbol for "fluoro" or "fluorinated").

Alternatively, the PFIB-alcohol adduct product may be fractionally distilled to produce a fraction which is predominately or consists essentially of the saturated adduct ether and a fraction which is predominately or consists essentially of unsaturated adduct ethers, and either fraction may be used as a starting material in the electrochemical fluorination reaction. The corresponding fluorinated compositions or products will comprise predominately the fully-fluorinated ether and predominately the partially-fluorinated ether (viz., said 2-hydryl compound), respectively.

The above-described electrochemical fluorination of the methanol adducts generally also produces surprisingly only small amounts (e.g., less than about 25 weight percent) of cleavage products, such as iso and normal $C_4F_{10}$ and $C_3F_8$ fluorocarbons (or "FCs"), along with $COF_2$.

Where ethanol adducts of PFIB are electrochemically fluorinated according to this invention, the perfluoroethyl ether homologs of the above-described perfluoromethyl ethers are produced along with a small amount of $C_5F_{12}$ fluorocarbon (e.g., less than about 5 weight percent).

The fluorinated products that are produced in accordance with this invention can be used per se in a host of applications requiring a thermally stable, inert medium, such as those applications where chlorofluorocarbons ("CFCs") or hydrochlorofluorocarbons (HCFCs") have been used. Such applications, for example, are as solvents for precision or metal cleaning of electronic articles such as disks or circuit boards, as working fluids, heat transfer agents, or coolants in refrigerator or freezer compressors or air conditioners, and as blowing agents in making polyurethane foam insulation.

A class of the adducts of perfluoro-olefin and aliphatic alcohols which can be used as organic starting materials in the electrochemical fluorination process of this invention are one or a mixture of compounds which can be represented by the general formula:

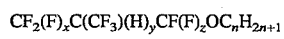
$$CF_2(F)_xC(CF_3)(H)_yCF(F)_zOC_nH_{2n+1} \qquad \text{I}$$

where:
  n is 1 to 4;
  x is zero or 1;
  y is zero or 1; and
  z is zero or 1;
with the provisos that when x is zero, then y is zero and z is 1; when x is 1 and y is 1, then z is 1; and when x is 1 and y is zero, then z is zero. Representative compounds of formula I are:

$$(CF_3)_2CHCF_2OCH_3 \qquad \text{Ia}$$

$(CF_3)_2CHCF_2OC_2H_5$      Ib $CF_2=C(CF_3)CF_2OCH_3$      Ic $CF_2=C(CF_3)CF_2OC_2H_5$      Id $(CF_3)_2C=CFOCH_3$      Ie $(CF_3)_2C=CFOC_2H_5$      If

Mixtures of such adducts can also be used as starting materials such as a mixture comprising a major amount (e.g., from 50 to 90 wt %) of Ia and a minor amount (e.g., 10 to 50 wt %) of Ie. But such mixtures can be fractionally distilled to produce fractions, each of which comprise predominantly a different one of such components, and each fraction may be used as the starting material to be electrochemically fluorinated.

The electrochemical fluorination reaction of this invention can be carried out by electrochemically fluorinating by the "Simons Process" a conductive solution of the organic starting material in anhydrous liquid hydrogen fluoride in an electrolytic cell. The fluorination product can be removed from the cell as part of the gaseous effluent. The effluent can be cooled to condense and collect or recover the aforementioned saturated and partially- or fully-fluorinated ethers. Any unreacted HF or HF by-product can also be condensed and recycled to the cell.

The "Simons process" or the "Simons electrochemical fluorination process" is a known, commercially-practical process for reacting anhydrous HF with certain classes of organic compounds. An early patent describing such technology is U.S. Pat. No. 2,519,983 (Simons), which contains a drawing of a Simons cell and its appurtenances, and a description and photograph of laboratory and pilot plant cells appear at pages 416–418 of Vol. 1 of "*Fluorine Chemistry*", edited by J. H. Simons, published in 1950 by Academic Press, Inc., New York. The aforementioned U.S. Pat. No. 3,962,348 (Benniger et al.) as well as U.S. Pat. No. 3,950,235 (Benniger) refer to the Simons process and Simons cell. Electrochemical fluorination by the Simons process is also described by S. Nagase in Fluorine Chem. Rev., 1 (1) 77–106(1967), and by T. Abe et al. in Chapter 1 of "Preparation, Properties, and Industrial Applications of Organofluorine Compounds," R. E. Banks, editor, Ellis Horwood Ltd., Holsted Press (1982).

Generally, in a relatively large-scale setting, a Simons cell useful in the practice of this invention comprises a cell body, typically made of carbon steel and usually provided with a cooling jacket, in which is suspended an electrode pack comprising series of alternating and closely-spaced cathode plates (typically made of iron, nickel, or nickel alloy) and anode plates (typically made of nickel), the plates being immersed in the current-conductive solution of the organic starting material in essentially anhydrous hydrogen fluoride. Gaseous cell effluent comprising the volatilized electrochemically fluorinated ether product and volatized hydrogen fluoride can be withdrawn from the cell as an overhead via a valved-outlet line. The cell is operated with the conductive solution containing a desired relative concentration of the organic starting material (the adduct of perfluoroolefin and alcohol) that will result in the production of the desired saturated, fully-fluorinated or partially-fluorinated product. And the relative temperatures and pressures underwhich the cell is operated will also be those conditions conducive to the production of the desired fluorinated product. Generally, by increasing the concentration of organic starting material in the conductive solution (and thereby decreasing the concentration of the HF reactant), the hydrogen-content of the resulting fluorinated products is increased, the reaction mixture in a sense being "starved" for HF. In order to produce an ECF product which contains a major amount of the 2-hydro fluorinated ethers, the concentration of HF in the conductive solution will generally be maintained at 50 to 75 wt %. And if the desired ECF product is one which is to contain a major amount of the fully-fluorinated (or perfluorinated) ether, the concentration of HF will generally be maintained at 75 to 99 wt %. Generally, the temperature of the cell during the electrochemical fluorination can be in the range of 20° to 70° C., preferably 50° to 60° C., which is above the boiling point of the fluorinated product (as well as hydrogen fluoride, which boils at about 20° C. at ambient pressure). In operation, the cell can be run at a pressure in the range of 0 to 65 psig (0 to $4.48\times10^5$ Pa) and preferably 5 to 45 psig ($0.34\times10^5$ to $3.10\times10^5$ Pa). The cell can be operated at average applied direct current cell voltages in the range of 4 to 9 volts, current densities in the range of 10 to 100, preferably 20 to 80, mAmp/cm$^2$ of active anode surface (where the electrolysis takes place). The cell can be operated either at constant current or constant voltage. The concentration of the organic starting material in the anhydrous hydrogen fluoride generally will be 5 to 20 weight percent. The reactor gaseous effluent, comprising the fluorinated adduct, hydrogen fluoride, hydrogen, and other gaseous products, can be withdrawn from the top of the reactor and passed to a condenser system, as described herein. Other details of the Simons electrochemical fluorination process and cell will be omitted here in the interest of brevity, and the disclosure of such technology in the above-cited references to such technology can be referred to for descriptions of such detail, which descriptions are incorporated herein for such purpose.

A class of the electrochemically-fluorinated compounds that can be produced in accordance with this invention can be represented by the general formula:

$$(CF_3)_2CRCF_2OC_nF_{2n+1} \quad \text{II}$$

where:

R is a fluorine atom or a hydrogen atom; and n is 1 to 4.

Representative compounds of formula II are:

$(CF_3)_2CHCF_2OCF_3$      IIa $(CF_3)_2CHCF_2OC_2F_5$      IIb $(CF_3)_2CFCF_2OCF_3$      IIc $(CF_3)_2CFCF_2OC_2F_5$      IId

The ECF product can also comprise mixtures of such compounds corresponding to the mixtures of the precursor adduct starting material mixtures. Those compounds of formula II where R is a hydrogen atom, viz., the 2-hydro compounds, are believed novel.

Objects and advantages of this invention are illustrated in the following examples. In these examples, a small scale or laboratory Simons cell and appurtenances were used.

EXAMPLE 1

In this example, the cell had a volume of about 180 cc and the electrode pack comprised alternating nickel anodes and cathodes comprising a total anode area of about 0.128 ft$^2$ (119 cm$^2$). The organic starting material was introduced into the top of the cell in essentially a continuous manner by a flexible gravity-feed conduit from a feed reservoir which was elevated during the run at a controlled rate corresponding to the current passed. The cell system was fitted with a stainless steel, HF condensation system which operated at about −40° to −45° C. and through which gases generated during the ECF process were passed, the system condensing the HF along with some of the desired fluorinated product. The condensed substances were allowed to split or separate in a product decanter into an upper phase comprising liquid HF and a lower liquid fluorinated phase. The liquid HF phase was returned to the cell. The uncondensed gases were passed through an HF-scavenger column filled with sodium fluoride particulate to remove HF traces, then passed through a tube containing silver fluoride catalyst to remove any $OF_2$ which might be produced, and then passed into a dry ice-cooled condenser-collection system to condense fluorinated product.

The ECF starting material or organic feed in the run of this example was a mixture comprising 74 wt % $(CF_3)_2CHCF_2OCH_3$, 15 wt % $(CF_3)_2C\!\!=\!\!CFOCH_3$, and 8 wt % $CF_2\!\!=\!\!C(CF_3)CF_2OCH_3$. The starting material was introduced into the ECF cell in batches of less than 1 vol % of the total electrolyte volume in order to maintain over the run high concentrations of HF to allow for maximum fluorination, that is, for perfluorination to take place. Over the length of an 80-hour run, 31 g of the starting material was fluorinated at atmospheric pressure, 19° C., and a steady 6.7 volts. Based on the starting material, a yield of about 50% of theoretical yield of $(CF_3)_2CFCF_2OCF_3$ was produced, viz., the liquid product combined from the −40° C. decanter and the dry ice collection system. The liquid product had a b.p. of 34°–35° C. A small amount of $(CF_3)_2CHCF_2OCF_3$ was also identified in the liquid product, that amount being about 10 wt % of the liquid or about 5% of said theoretical yield. Analysis of the cleavage products by gas chromatography Fourier transform infra red (GC-FTIR) and gas chromatography-mass spectra (GC-MS) showed the liquid product to contain small amounts of iso-$C_4F_{10}$, $(CF_3)_2CFCOF$, $C_3F_8$, $COF_2$, and $CF_4$. No PFIB, $(CF_3)_2C\!\!=\!\!CF_2$, was found in the cell product and it had only a minor amount of starting material.

EXAMPLE 2

The run of Example 1 was repeated at higher temperature and higher pressure in a similar ECF cell that was equipped with a back-pressure control valve system which allowed the cell to be operated at greater than atmospheric pressure, namely, from 1 psig ($0.069\times10^5$ Pa) to up to 20 psig ($1.38\times10^5$ Pa). The fluorination was carried out at 5.6 volts while running at about 1.0 amps/hr., 30° C., and 10 psig ($0.69\times10^5$ Pa) back-pressure. The starting material feed-rate corresponded to about 105% of the theoretical current necessary to displace the hydrogen atoms in the starting material, based upon the current passed through the conductive solution in the cell; this feed-rate allowed the HF concentration in the solution to decrease from essentially 100% down to 90% over the course of the run. Consequently, the amount of the hydryl ether, $(CF_3)_2CHCF_2OCF_3$, produced was greater, namely, about 1 part per 3 parts of the fully-fluorinated ether, $(CF_3)_2CFCF_2OCF_3$.

EXAMPLE 3

In this example a Simons cell (of the type described in U.S. Pat. No. 2,713,593) was provided with a gravity-feed and condensation systems like that used in Example 1. The cell held a volume of conductive solution of about 1500 cc and was used to fluorinate $(CF_3)_2CHCF_2OCH_3$, a starting material which was about 99% pure. The ECF of this run was carried out at 5.5 to 7.0 volts and at various currents ranging from 5.0 to 35 amps. Cell pressures ranged from 0 to 20 psig (0 to $1.38\times10^5$ Pa) control, and temperatures ranged from 0° to 45° C. During the course of the 221-hour run, 2490 g of the starting material was essentially continuously fed, as in Example 2, into the cell at a rate that maintained the average current density of 0.015 amps/$cm^2$. The condensed liquid product, collected and combined from the decanter and dry ice-cooled collection system, was analyzed and found to have as its major component the fully-fluorinated ether, $(CF_3)_2CFCF_2OCF_3$, the amount of which was produced at about 30% of the theoretical yield, and the liquid product was found to have a lesser amount of the partially-fluorinated ether, $(CF_3)_2CHCF_2OCF_3$, the amount of which was produced at an average of about 25 to 30% of the theoretical amount of the fully-fluorinated ether. In the course of the run, the ECF operation could be varied in such a manner that the ratio of formation of the fully-fluorinated ether to the partially-fluorinated ether could be decreased from about 10:1 down to 1:1. This decreased ratio was obtained by decreasing the HF concentration of the conductive solution from about 99% down to about 70% while (1) simultaneously keeping cell temperatures down to less than the normal boiling point of HF at the respective pressure the cell was being operated at, and (2) while maintaining an essentially constant addition of starting material to the cell such that the concentration of electrolyte was not allowed to drop below about 20 to 30%. Increasing the current required higher voltages and generally resulted in more cleavage products with chain lengths of less than 5 carbons and in a drop in the ratio of the partially-fluorinated product to the fully-fluorinated product.

The amount of collected liquid product was about 2600 g and it was subjected to fractional distillation using a 20-tray Oldershaw column equipped with a variable reflux splitter. Eighteen different distillation cuts or fractions were made, the total received being about 2300 g. GC-FTIR analyses were run on each of the cuts to determine purity, and GC-MS and fluorine-19 nuclear magnetic reasonance ($^{19}F$ NMR) analyses were run on some of the cuts to determine chemical structure. The principle products and their boiling points and yields (as % of the theoretical amount of the fully-fluorinated ether) were as follows:

| Component | b.p., °C. | Yield, % of theoretical |
| --- | --- | --- |
| $(CF_3)_2CFCF_2OCF_3$ | 33 | 35 to 40 |
| $(CF_3)_2CHCF_2OCF_3$ | 46 | 25 to 30 |
| $(CF_3)_2CFCOF$ | 0 | 5 to 10 |
| $(CF_3)_2CHCOF$ | 15 | 5 |
| $(CF_3)_2CFCF_3$ | 0 | 5 to 10 |
| $(CF_3)_3CH$ | 12 | 10 to 15 |
| $(CF_3)_2CHOCHF_2 +$ $(CF_3)_2CHOCH_2F$ | — | <5 |
| $(CF_3)_2CHCF_2OCH_3$ | 69.5–70 | 5 |

EXAMPLE 4

In this example, an ethanol adduct of PFIB was fluorinated in an ECF cell of the type used in Example 2. The adduct starting material was a mixture of 66 wt % $(CF_3)_2CHCF_2OC_2H_5$ and 33% wt % $(CF_3)_2C\!\!=\!\!CFOC_2H_5$ (formed by the elimination of HF from the foregoing 2-hydryl compound). The cell voltage was held constant at 6.0 volts with an average current of 1.16 amps for 58.5 hours of running time. The condensed organic liquids were collected from the decanter and dry ice-cooled condenser and combined as a liquid product and analyzed using GC-FTIR and GC-MS. The liquid product was found to be a mixture of a major amount of $(CF_3)_2CFCF_2OC_2F_5$, and a somewhat lesser amount of $(CF_3)_2CHCF_2OC_2F_5$, the ratio of the former to the latter being about 11:7. The liquid product contained even lesser amounts of other hydrogen-containing compounds. The cleavage products from the fluorination were similar to those found for the ECF product produced in the Example 1 from the methanol adduct starting material.

Various modifications and alterations of this invention will be apparent to those skilled in the art without departing from the scope and spirit of this invention.

What is claimed is:

1. A process for the production of fluoro-alkyl fluoro-isobutyl ether product that comprises fluorinating in an electrochemical cell an electrically conductive solution comprising an adduct of perfluoro-isobutene and aliphatic alcohol in anhydrous hydrogen fluoride wherein the concentration of anhydrous hydrogen fluoride in the conductive solution is maintained between approximately 50 and 70 weight percent and the electrochemical cell is under temperature and pressure conditions sufficient to produce a major amount of 2-hydro fluorinated ether product.

2. The process of claim 1 wherein said adduct which is fluorinated is one or a mixture of compounds represented by the general formula:

$$CF_2(F)_xC(CF_3)(H)_yCF(F)_zOC_nH_{2n+1} \qquad I$$

where:

n is 1 to 4;

x is zero or 1;

y is zero or 1; and z is zero or 1;

with the provisos that when x is zero, then y is zero and z is 1; when x is 1 and y is 1, then z is 1; and when x is 1 and y is zero, then z is zero.

3. The process of claim 1 wherein said adduct which is fluorinated comprises a mixture of $(CF_3)_2CHCF_2OCH_3$ and $(CF_3)_2C=CFOCH_3$, and $CF_2=C(CF_3)CF_2OCH_3$.

4. The process of claim 1 wherein said adduct which is fluorinated comprises a mixture of $(CF_3)_2CHCF_2OC_2H_5$ and $(CF_3)_2C=CFOC_2H_5$, and $CF_2=C(CF_3)CF_2OC_2H_5$.

5. A process for the production of fluoro-alkyl fluoro-isobutyl ether product that comprises fluorinating in an electrochemical cell an electrically conductive solution comprising an adduct of perfluoro-isobutene and aliphatic alcohol in anhydrous hydrogen fluoride wherein the concentration of anhydrous hydrogen fluoride in the conductive solution is maintained between approximately 75 and 99 weight percent and the electrochemical cell is under temperature and pressure conditions sufficient to produce a major amount of fully-fluorinated fluoro-alkyl fluoroisobutyl ether product and a minor amount of a 2-hydro fluorinated ether product.

6. The process of claim 5 wherein said adduct which is fluorinated is one or a mixture of compounds represented by the general formula:

$$CF_2(F)_xC(CF_3)(H)_yCF(F)_zOC_nH_{2n+1} \qquad I$$

where:

n is 1 to 4;

x is zero or 1;

y is zero or 1; and z is zero or 1;

with the provisos that when x is zero, then y is zero and z is 1; when x is 1 and y is 1, then z is 1; and when x is 1 and y is zero, then z is zero.

7. The process of claim 5 wherein said adduct which is fluorinated comprises a mixture of $(CF_3)_2CHCF_2OCH_3$ and $(CF_3)_2C=CFOCH_3$, and $CF_2=C(CF_3)CF_2OCH_3$.

8. The process of claim 5 wherein said adduct which is fluorinated comprises a mixture of $(CF_3)_2CHCF_2OC_2H_5$ and $(CF_3)_2C=CFOC_2H_5$, and $CF_2=C(CF_3)CF_2OC_2H_5$.

* * * * *

UNITED STATES PATENT AND TRADEMARK OFFICE
CERTIFICATE OF CORRECTION

PATENT NO.: 5,474,657

DATED: December 12, 1995

INVENTOR(S): John C. Hansen

It is certified that error appears in the above-identified patent and that said Letters Patent is hereby corrected as shown below:

Col. 1, line 14, delete [(CF$_3$)2] and insert therefore --(CF$_3$)$_2$--.

Col. 1, line 16, delete [2-hydryl-2 -(fluoromethyl)] and insert therefore --2-hydryl-2-(fluoromethyl)--.

Col. 2, line 3, delete [(perfluoromethyl)-1 -propenyl] and insert therefore --(perfluoromethyl)-1-propenyl--.

In the table in Col. 6, line 56, please correct the line to read as follows:

(CF$_3$)$_2$CHOCHF$_2$+

In the table in Col. 6, line 57, please correct the line to read as follows:

(CF$_3$)$_2$CHOCH$_2$F     --    <5

Signed and Sealed this

Ninth Day of July, 1996

Attest:

BRUCE LEHMAN

Attesting Officer      Commissioner of Patents and Trademarks